US006939549B2

(12) United States Patent
de la Fuente et al.

(10) Patent No.: US 6,939,549 B2
(45) Date of Patent: *Sep. 6, 2005

(54) IMMUNOPROTECTIVE RECOMBINANT ANTIGEN FROM ANAPLASMA MARGINALE, VACCINE COMPOSITIONS AND METHODS OF USE

(75) Inventors: Jose de Jesus de la Fuente, Stillwater, OK (US); Katherine M. Kocan, Perkins, OK (US); Jose Carlos Garcia-Garcia, Stillwater, OK (US); Edmour F. Blouin, Perkins, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/002,636

(22) Filed: Oct. 26, 2001

(65) Prior Publication Data

US 2002/0127242 A1 Sep. 12, 2002

Related U.S. Application Data

(60) Provisional application No. 60/244,333, filed on Oct. 30, 2000.

(51) Int. Cl.$^7$ ...................... A61K 39/00; A61K 39/002; A61K 39/38; A01N 63/00; A01N 65/00
(52) U.S. Cl. ............................... 424/265.1; 424/266.1; 424/184.1; 424/191.1; 424/93.1
(58) Field of Search ......................... 424/184.1, 235.1, 424/265.1, 191.1, 269.1, 266.1, 93.1, 93.4

(56) References Cited

U.S. PATENT DOCUMENTS

| | | | |
|---|---|---|---|
| 3,674,860 A | * | 7/1972 | Welter et al. |
| 4,956,278 A | | 9/1990 | Hart et al. ................. 435/30 |
| 5,549,898 A | | 8/1996 | McGuire et al. ......... 424/269.1 |
| 5,798,219 A | | 8/1998 | Knowles et al. ........... 435/7.93 |
| 5,869,335 A | | 2/1999 | Munderloh et al. ......... 435/348 |
| 6,025,338 A | | 2/2000 | Barbet et al. ................. 514/44 |
| 6,242,571 B1 | * | 6/2001 | Knowles et al. |
| 2002/0127242 A1 | * | 9/2002 | de la Fuente et al. |

FOREIGN PATENT DOCUMENTS

| | | | |
|---|---|---|---|
| EP | 196290 | * | 10/1986 |
| WO | WO 97/08296 | * | 3/1997 |
| WO | WO 03/093416 A2 | * | 11/2003 |

OTHER PUBLICATIONS

Garcia–Garcia et al, Vet. Immunology and Immunopathology, 2004, 98:137–151.*
de la Fuente et al, J. Applied Research in Vet. Med., 2003, 1/4:285–292.*
Blouin et al, Vet. Parasitology, Feb. 2003, 111/2–3:247–260.*
de la Fuente et al, Vet. Microbiology, Oct. 2002, 89/2–3:239–251.*
Kocan et al, Experimental and Applied Acaralogy, 2002, 28/1–4:9–25.*
Camacho–Nuez et al Infection & Immunity 68/4: 1946–1952, Apr. 2000.*
Brown et al, Infection & Immunity 66/11: 5414–5422, Nov. 1998.*
Palmer et al Infection & Immunity 50/3: 881–886, Dec. 1985.*
Arulkanthan et al, Infection & Immunity 67/7: 3481–3487, Jul. 1999.*
McGuire etal, Vaccine, 12/5: 465–471, 1994.*
Bowie etal, Gene, 282: 95–102, 2002.*
Brown etal, Infection & Immunity 69/11: 6853–6862, Nov. 2001.*
de la Fuente etal, International J Parasitology 31: 1705–1714, 2001.*
Palmer et al, Parasitology Today 15/7: 281–286, 1999.*
Vidotto et al, Infection and Immunity, 62/7: 2940–2946, Jul. 1994.*
McGarey DJ, Barbet AF, Palmer GH, McGuire TC, Allred Dr. Putative adhesins of *Anaplasma marginale*: major surface polypeptides 1a and 1b. Infect Immun 1994; 62: 4594–4601.
Munderloh UG, Blouin EF, Kocan KM, Ge NL. Establishment of the tick (Acari: Ixodidae)–borne cattle pathogen *Anaplasma marginale* (Rickettsiales: *Anaplasmataceae*) in tick cell culture. J Med Ent 1996; 33: 656–664.
Oberle SM, Palmer GH, Barbet AF, McGuire TC. Molecular size variations in an immunoprotective protein complex among isolates of *Anaplasma marginale*. Infect Immun 1988; 56: 1567–1573.
Palmer GH, Barbet AF, Cantor GH, McGuire TC. Immunization of cattle with the MSP–1 surface protein complex induces protection against a structurally variant *Anaplasma marginale* isolate. Infect Immun 1989; 57: 3666–3669.
Palmer GH, McElwain TF. "Molecular basis for vaccine development against *anaplasmosis* and *babesiosis*." Vet Parasitol: 1995; 57: 233–253.
Palmer GH, Waghela SD, Barbet AF, Davis WC, McGuire TC. Characterization of a neutralization–sensitive epitope on the AM 105 surface protein of *Anaplasma marginale*. J Parasitol 1987: 17: 1279–1285.
Viseshakul N, Kamper S, Bowie MV, Barbet AF. Sequence and expression analysis of a surface antigen gene family of the rickettsia *Anaplasma marginale*. Gene 2000; 253: 45–53.

(Continued)

*Primary Examiner*—Nita Minnifield
(74) *Attorney, Agent, or Firm*—Fellers, Snider, Blankenship, Bailey & Tippens, P.C.

(57) ABSTRACT

Vaccines and methods useful to induce an immune response which is protective to reduce the severity or prevent infection by ehrlichial parasites of the species *Anaplasma marginale* utilizing recombinant MSP1a surface protein antigens alone or in combination with tick cell culture derived *A. marginale*.

13 Claims, 1 Drawing Sheet

OTHER PUBLICATIONS

Allred DR, McGuire TC, Palmer GH, Leib SR, Harkins TM, McElwain TF, Barbet AF. Molecular basis for surface antigen size polymorphisms and conservation of a neutralization–sensitive epitope in Anaplasma marginale. Proc Natl Acad Sci USA 1990; 87: 3220–3224.

Barbet AF, Blentlinger R, Jooyoung Y, Lundgren AM, Blouin EF, Kocan KM. Comparison of surface proteins of Anaplasma marginale grown in tick cell culture, tick salivary glands, and cattle. Infect Immun 1999; 67: 102–107.

Barbet AF, Palmer GH, Myler PJ, McGuire TC. Characterization of an immunoprotective protein complex of Anaplasma marginale by cloning and expression of the gene coding for polypeptide AM 105L. Infect Immun1987; 55: 2428–2435.

Blouin EF, Barbet AF, Jooyoung Y, Kocan KM, Saliki JT. Establishment and characterization of an Oklahoma isolate of Anaplasma marginale in cultured Ixodes scapularis cells. Vet Parasitol 1999; 87: 301–313.

Blouin EF, Kocan KM. Morphology and development of Anaplasma marginale (Rickettsiales: Anaplasmataceae) in cultured Ixodes scapularis (Acari:Ixodidae) cells. J Med Entomol 1998; 35: 788–797.

De la Fuente J, Garcia–Garcia JC, Blouin EF, Kocan KM. Differential adhesion of major surface proteins 1a and 1b of the ehrlichial cattle pathogen Anaplasma marginale to bovine erythrocytes and tick cells. Int. J. Parasitol. 2001; 31: 145–153.

De la Fuente J, Van Den Bussche RA, Kocan KM. Molecular phylogeny and biogeography of North American isolates of Anaplasma marginale (Rickettsiaceae: Ehrlichieae). Vet Parasitol 2001; 97: 65–76.

Kocan KM, Blouin EF, Barbet AF. Anaplasmosis control: past, present and future. Ann NY Acad Sci, 2000; 916: 501–509.

McGarey DJ, Allred DR. Characterization of hemagglutinating components on the Anaplasma marginale initial body surface and identification of possible adhesins. Infect Immun 1994; 62: 4587–4593.

PCT International Search Report. PCT/US01/48505. p. 1–5.

Arulkanthan, Appudurai, et al. Biased Immunoglobulin G1 Isotype Responses Induced in Cattle with DNA Expresing msp 1a of Anaplasma marginale. Infection and Immunity, Jul. 1999, p. 3481–3487.

Almazan et al., 2003 Vaccine 21:1492–1501.

Blouin et al., Antibodies to Anaplasma Marginale Major Surface Protein 1A and 1B Inhibit Infectivity for Cultured Tick Cells, 2002b Veterinary Parasitology 111:247–260.

de la Fuente et al., Characterization of the Functional Domain of Major Surface Protein 1A Involved in Adhesion of the Rickettsia Anaplasma Marginale to Host Cells, 2003 Veterinary Microbiology 91:265–283.

de la Fuente et al., Evolution and Function of Tandem Repeats in the Major Surface Protein 1A of the Ehrlichial Pathogen Anaplasma Marginale, 2001a An. Health Res. Rev. 2:2:163–173.

de la Fuente et al., 2003 Expert Rev. Vaccines 2/4:583–593.

de la Fuente et al., 2002 Vet. Microbiology 89:239–251.

Eid et al., Expression of Major Surface Protein 2 Antigenic Variants During Acute Anaplasma Marginale Rickettsemia, 1996 Infect. Immun. 64:836–841.

Kocan et al., Immunization of Cattle with Anaplasma Marginale Derived from Tick Cell Culture, 2001 Vet. Parasitol 102: 151–161.

Kocan, Development of Anaplasma Marginale: Coordinated Development of a Rickettsial Organisms and Its Tick Host, 1986 Morphology, Physiology and Behavioral Ecology of Ticks Chichester, Horwood, pp. 472–505.

Kocan, Preliminary Studies on the Effect of Anaplasma Marginale Antibodies Ingested by Dermacentor Andersoni Ticks (Acari: Ixodidae) with Their Bloodmeal on Infections in Salivary Glands, 1996 Exp. Acarol. 20:297–311.

Montenegro–James et al., Efficacy of Purified Anaplasma Marginale Initial Bodies as a Vaccine Against Anaplasmosis, 1991 Parasitol. Res. 77:93–101.

Palmer et al., Strain Composition of the Ehrlichia Anaplasma Marginale Within Persistently Infected Cattle, a Mamalian Reservoir for Tick Transmission, 2001 J. Clin. Microbiol. 39:631–635.

* cited by examiner

IMMUNOPROTECTIVE RECOMBINANT ANTIGEN FROM ANAPLASMA MARGINALE, VACCINE COMPOSITIONS AND METHODS OF USE

CROSS REFERENCE TO RELATED APPLICATION

This application claims the benefit of prior filed, copending U.S. provisional patent application Ser. No. 60/244,333, filed Oct. 30, 2000, which application is hereby incorporated by reference.

BACKGROUND OF THE INVENTION

1. Technical Field

The present invention relates to antigenic polypeptides and proteins, related vaccines and methods useful to induce an immune response which is protective to reduce the severity or prevent infection by ehrlichial parasites of the species *Anaplasma marginale*.

2. Background

Anaplasmosis is a tick-borne disease of cattle caused by the obligate intraerythrocytic ehrlichial pathogen *A. marginale*. The acute phase of the disease is characterized by severe anemia, weight loss, fever, abortion, lower milk production and often death. The only known site of development of *A. marginale* in cattle is within bovine erythrocytes. The number of infected erythrocytes increases logarithmically and removal of these infected cells by phagocytosis results in development of anemia and icterus without hemoglobinemia and hemogloinuria. Biological transmission of *A. marginale* is effected by feeding ticks, while mechanical transmission occurs when infected blood is transferred to susceptible animals by biting flies or by blood-contaminated fomites. Cattle that recover from acute infection remain persistently infected and serve as reservoirs for mechanical transmission and infection of ticks. Approximately 20 species of ticks have been incriminated as vectors worldwide. The developmental cycle of *A. marginale* in ticks is complex and coordinated with the tick feeding cycle. After infection and development of *A. marginale* in tick gut cells, many other tick tissues become infected, including the salivary glands from where the ehrlichia is transmitted to vertebrates during feeding.

MSP1 is one of six major surface proteins (MSPs) that have been described on *A. marginale* from bovine erythrocytes and has been found to be conserved on tick salivary gland-derived *A. marginale* [1]. MSP1 is a heterodimer composed of two structurally unrelated polypeptides: MSP1a which is encoded by a single gene, msp1α, and MSP1b which is encoded by at least two genes, msp1β1 and msp1β2 [2, 3]. MSP1a is variable in molecular weight among geographic isolates because of a variable number of tandem 28 or 29 amino acid repeats in the amino terminal of the protein. Immunization of cattle with affinity-purified native MSP1 complex has previously been shown to induce protective immunity in cattle that received homologous or heterologous challenge with *A. marginale* geographic isolates [4, 5]. In addition, MSP1a and MSP1b expressed by recombinant *Escherichia coli* were shown to be putative adhesins to bovine erythrocytes [6, 7]. Although the MSP1 complex has been suggested to be involved in erythrocyte invasion, its role in infection and multiplication of the parasite in the tick vector has not been reported.

Recently, *A. marginale* has been grown in continuous culture in a cell line, IDE8, derived from embryos of the tick *Ixodes scapularis* [8]. See also U.S. Pat. No. 5,869,335, incorporated herein by reference. The Virginia isolate of *A. marginale* was initially propagated in the IDE8 tick cell line but subsequently an Oklahoma isolate was propagated in the tick cell line and characterized [9]. Colonies of *A. marginale* in cultured tick cells were morphologically similar to those observed in ticks [8–10], and *A. marginale* harvested from cell culture were infective for both cattle and ticks. All 6 MSPs of *A. marginale* were found to be conserved on the cell culture-derived organisms and the antigenic composition remained the same after successive passage in cell culture. The *A. marginale* isolate antigenic identity, as determined by the molecular weight of the MSP1a, was retained in culture [9, 11].

MSP1 complex isolated *A. marginale* also has been utilized for the vaccination of ruminants, as disclosed by McGuire et al. in U.S. Pat. No. 5,549,898 issued Aug. 27, 1996 (said patent being incorporated herein by reference).

Existing vaccines, however, including formulations using partially purified parasites from infected erythrocytes and cultured tick cells, are currently handicapped by mechanisms developed by the parasite to hide the most relevant epitopes from the host immune system. The inclusion of recombinant protein preparations in vaccine formulations would allow the development of host immune response against relevant epitopes not available for the host immune system in natural conformations present in whole-parasite or parasite-derived purified antigens.

SUMMARY OF THE INVENTION

Experimental results described by the inventors in copending U.S. provisional patent application Ser. No. 60/244,333 demonstrate a differential role for MSP1a and MSP1b polypeptides of the MSP1 surface protein complex for adherence of *A. marginale* to bovine erythrocytes and tick cells. Recombinant MSP1a expressed in *E. coli* was shown to be an adhesin for bovine erythrocytes and both native and cultured tick cells. In contrast, recombinant *E. coli* expressing MSP1b adhered only to bovine erythrocytes and not to tick cells. The role of the MSP1 complex, therefore, was determined to vary among vertebrate and invertebrate hosts.

The present invention is based upon the surprising discovery that cattle immunized with the recombinant MSP1a surface protein antigen of the MSP1 complex alone or in combination with tick cell culture-derived *A. marginale* are better protected against *A. marginale* infection as demonstrated by a lower reduction in packed cell volume (PCV) and lower peak parasitemia (PPE) than cattle immunized with the MSP1 complex, a combination of uncomplexed MSP1a and MSP1b surface protein antigens, the MSP1b antigen alone, cell culture derived *A. marginale*, or cell culture derived *A. marginale* combined with MSP1b. Indeed, only erythrocyte-derived *A. marginale* appears to confer like protection.

Thus, in one embodiment of the present invention there is provided a vaccine composition for inducing an immune response in a ruminant, the vaccine composition comprising the recombinant MSP1a purified surface protein antigen of *A. marginale* or subunits thereof, alone or in combination with other antigenic components, wherein the vaccine composition further comprises a pharmaceutically acceptable carrier or diluent.

In another embodiment of the present invention there is provided, a method for inducing an immune response in a ruminant to provide immune protection which reduces the severity of or prevents infection by *A. marginale*, the method comprising administering to said ruminant an effective amount of the inventive vaccine composition.

A better understanding of the present invention, its several aspects, and its advantages will become apparent to those skilled in the art from the following detailed description, taken in conjunction with the attached figures, wherein there is described the preferred embodiment of the invention, simply by way of illustration of the best mode contemplated for carrying out the invention.

DETAILED DESCRIPTION OF THE INVENTION

Figure 1:
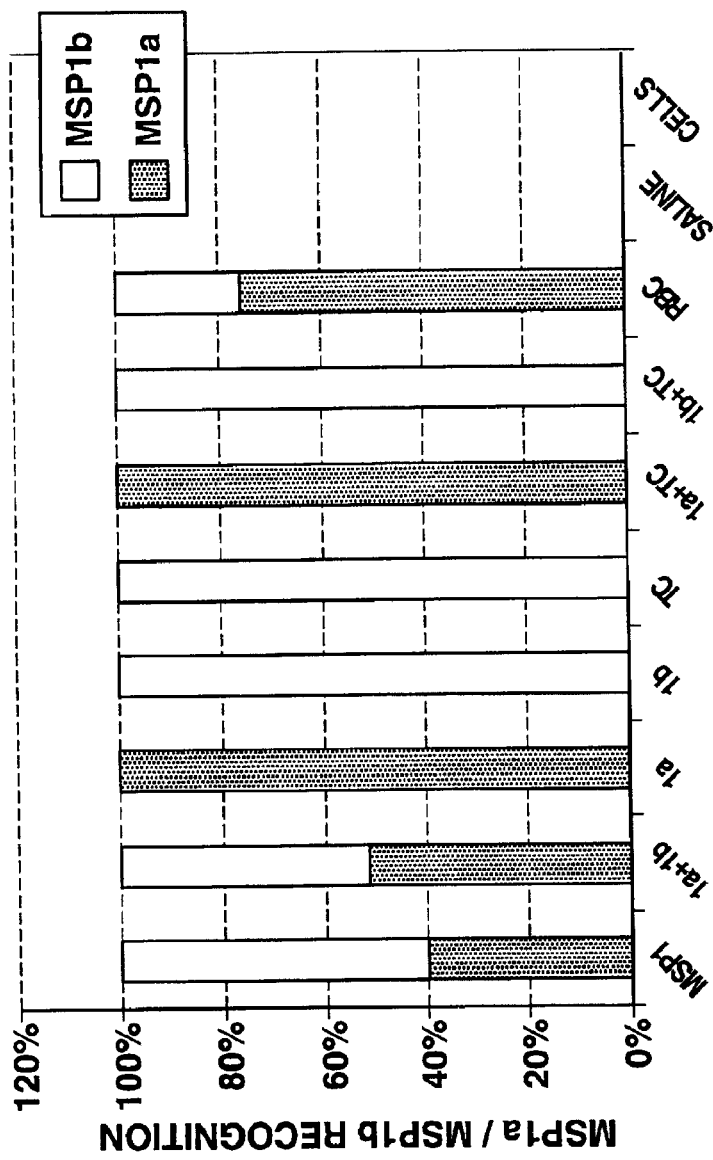
FIG. 1 is a graphical illustration of the immune response against MSP1a and MSP1b determined by Western blot analysis of sera derived from immunized cattle and controls generated in connection with the experimental results reported herein.

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

In accordance with the present invention there is provided a new vaccine against the ehrlichial cattle pathogen *A. marginale* through the use of discrete recombinant MSP1a and polypeptides derived from MSP1a containing the immunoprotective and functional regions that are expressed in *E. coli*. In one aspect, only recombinant MSP1a or immunoprotective and functional regions thereof are utilized as the antigenic component of the vaccine. In another aspect, recombinant MSP1a or subunits thereof are utilized in combination with other antigen preparations, particularly antigen preparations derived from *A. marginale*-infected cultured tick IDE8 cells.

MSP1a and MSP1b are isolated from *A. marginale* initial bodies as a complex of two noncovalently linked, antigenically distinct polypeptides. It is possible that the association between MSP1a and MSP1b in the surface protein complex allows the parasite to more effectively bind to erythrocyte and/or tick cell components. MSP1a could be the essential subunit in the recognition of the tick cell receptor, while the binding to the erythrocyte receptor could be mediated primarily by MSP1b or by both protein subunits through the binding of distinct erythrocyte components. Additionally, the association between MSP1a and MSP1b could stabilize and/or properly conform the MSP1 complex [6].

MSP1a is encoded by a single monocystronic gene, msp1α, which is polymorphic among geographical isolates of *A. marginale* [12, 13, 15]. *A. marginale* isolates differ in the number of 28–29 amino acids tandem repeats within the MSP1a polypeptide [13, 15], which contain a neutralization-sensitive epitope [4, 13]. However, the sequence of msp1α does not change during the multiplication of the parasite in the bovine host and the tick vector. The second MSP1 subunit, MSP1b, is encoded by at least two monocystronic genes, msp1β1 and msp1β2 [3]. These loci are polymorphic between and within populations of *A. marginale* from different geographical regions and life cycle stages but conserve a high degree of similarity. Sequence diversity is mainly due to point mutations in variable regions, perhaps due to selective immune pressure. The genetic structure of msp1 α and β genes together with the vital function of codified polypeptides permits the inclusion of recombinant MSP1 polypeptides, or its functional domains, in vaccine formulations against *A. marginale*.

The experiments described and examples provided hereinafter demonstrate that cattle immunized with recombinant MSP1a alone or in combination with tick cell culture derived *A. marginale* are unexpectedly better protected against *A. marginale* infection as demonstrated by a lower reduction in packed cell volume (PCV) and lower peak parasitemia (PPE) than cattle immunized with the MSP1 complex, a combination of uncomplexed MSP1a and MSP1b surface protein antigens, the MSP1b antigen alone, cell culture derived *A. marginale*, or cell culture derived *A. marginale* combined with MSP1b. Indeed, only erythrocyte-derived *A. marginale* appears to confer like protection.

EXAMPLE 1

Preparation of Recombinant *E. coli* Expressing MSP1 α and Preparation of Antigen The msp1 α gene was cloned by PCR from the Oklahoma isolate of *A. marginale* derived from infected erythrocytes. DNA was extracted from 1 ml stored blood samples containing infected bovine erythrocytes collected during high parasitemia employing 250 µL Tri Reagent (Sigma) and following manufacturer's recommendations. Extracted DNA was resuspended in 100 µL water. The msp1α gene was amplified from 1 µL DNA by PCR using 10 pmol of each primer MSP1aP: 5'GCATTACAACGCAACGCT-TGAG3' (SEQ. ID NO: 1) and MSP1a3: 5'GCTTTACGC-CGCCGCCTGCGCC3' (SEQ. ID NO: 2) in a 50-µL volume PCR employing the Access RT-PCR system (Promega). Reactions were performed in an automated DNA thermal cycler (Eppendorf) for 35 cycles. After an initial denaturation step of 30 sec at 94° C., each cycle consisted of a denaturing step of 30 sec at 94° C. and an annealing-extension step of 2.5 mm at 68° C. The program ended by storing the reactions at 40° C. PCR products were electrophoresed on 1% agarose gels to check the size of amplified fragments. The amplified fragments were resin purified from PCR reactions (Wizard Promega) and cloned into pGEM-T vector (Promega) for sequencing both strands (Core Sequencing Facility, Department of Biochemistry and Molecular Biology, Noble Research Center, Oklahoma State University).

For high level expression of MSP1a, msp1α coding region was amplified from per1 (msp1α in pGEM-T vector) plasmid DNA by PCR using the primers 5'CCGCTC-GAGATGTAGCGGAGTATGTGTCC3' (SEQ. ID NO: 3) and 5'GAAGATCTCGCCGCCGCCTGCGCC3' (SEO. ID NO: 4). The msp1α amplification product was digested with XhoI and BglII and inserted into the cloning site of pFLAG-CTC expression vector (Sigma). Recombinant plasmid was named pFLC1 a. In this construct, the inserted gene is under the control of the inducible tac promoter and yield full-length MSP1a polypeptide, with a C-terminal fusion of a FLAG marker octapeptide. The fidelity and orientation of the construct was verified by sequencing. For expression of MSP1a recombinant polypeptides, pFLC1a expression plasmid was transformed into *E. coli* K-12 (strain JM109). Transformed *E. coli* strains were inoculated in LB containing 50 µg/ml Ampicillin and 0.4% glucose. Cultures were grown at 37° C. to $OD_{600\ nm}=0.4$. IPTG was then added to 0.5 mM final concentration, and incubation continued during 4 h, for induction MSP1a expression. Cells were collected by centrifugation and membranes extracted after sonication and centrifugation. MSP1b was cloned, expressed and purified in a similar way. Doses of 5 ml containing 100 µg recombinant antigens were used for vaccination in subsequent studies.

EXAMPLE 2

Analysis of the Protective Capacity of Vaccine Preparations Containing Recombinant MSP1a 1. Propagation of *Anaplasma marginale* in tick cell culture and preparation of immunogen. The IDE8 (ATCC CRL 11973) tick cell line derived from embryos of *Ixodes scapularis* was maintained at 31° C. in L-15B medium, pH 7.2, supplemented with 5% heat inactivated fetal bovine serum (FBS; Sigma, USA), 10% tryptose phosphate broth (Difco, USA) and 0.1% bovine lipoprotein concentrate (ICN, USA). Cultures were grown in 25-$cm^2$ plastic flasks (Nunc, Rosekilde, Denmark) with 5 ml of medium, and the medium was replaced weekly. The cells were subcultured at 1:5 to 1:20, and the cells became tightly adherent to the culture substrate and multiplied with a population doubling time of 3 to 5 days to a density of about $5 \times 10^6$ cells/ml. Nearly confluent monolayers from each passage were collected and stored in liquid nitrogen in medium with 10% DMSO.

Tick cell cultures infected with the Oklahoma isolate of *A. marginale* were propagated. Terminal cell cultures were harvested, the cells centrifuged, and the contents of each T25 flask was resuspended in 1 ml PBS and stored at −70° C. until used as antigen for immunogen doses. The antigen aliquots were thawed, pooled and a sample was taken and tested by indirect ELISA. The cell culture-derived antigen was inactivated with beta propiolactone (BPL) and the volume was adjusted to 5 ml so that each dose contained approximately $2 \times 10^{10}$ *A. marginale*.

2. Preparation of *A. marginale* antigen from bovine erythrocytes. Two susceptible, splenectomized calves (PA432 and PA433) were each inoculated with 2.5 ml blood stabilate (40% parasitemia) collected from a calf with the Virginia isolate of *A. marginale*. The calves were monitored for infection by examination of stained blood smears. Blood was collected from PA432 at parasitemias of 13.6% and 32.7% and from PA433 at parasitemias of 12.2% and 12.9%. After each collection, the erythrocytes were washed 3 times in PBS, each time removing the buffy coat. The erythrocytes were frozen at −70° C. 1:1 in RPMI cell culture medium until used as antigen for the immunization studies. The frozen erythrocyte antigen was thawed, washed in PBS, and centrifuged. The resulting pellet was washed to remove the hemoglobin, after which the antigen was pooled and inactivated with BPL. An aliquot was tested by ELISA as described previously for the erythrocyte antigen preparation using a known erythrocyte standard. Doses (5 ml) were prepared that contained approximately $2 \times 10^{10}$ *A. marginale*.

3. Experimental design. Fifty, 16-month month old Angus cattle were randomly assigned into ten groups of five cattle each that were immunized with various antigens as follows. (1) MSP1 complex, (2) MSP1a and MSP1b, (3) MSP1a, (4) MSP1b, (5) cell culture-derived *A. marginale*, (6) cell culture-derived *A. marginale* and MSP1a, (7) cell culture-derived *A. marginale* and MSP1b, (8) erythrocyte-derived *A. marginale*, (9) uninfected IDE8 tick cells and (10) adjuvant only.

4. Immunizations. All cattle were immunized 3 times by subcutaneous injection of the antigen at weeks 1, 4 and 6. Each antigen dose was 5 ml in volume and contained an antigen in the adjuvant, XTEND® III (Grand Laboratories, Larchwood, Iowa). All cattle were challenge-exposed 10 weeks after the last immunization with $1 \times 10^7$ *A. marginale* infected erythrocytes collected from a calf experimentally infected with the Oklahoma isolate of *A. marginale*. Blood of the immunized and control cattle was monitored for infection with *A. marginale* by microscopic examination of blood smears and hematology was done daily after the onset of infection. Parameters evaluated in cattle included determination of the peak percent infected erythrocytes (PPE), percent reduction in the packed cell volume (PCV), and the prepatent period (days) determined from the day of challenge-exposure to the onset of infection.

5. Collection of blood and serum samples. Whole blood was collected in vacutainer tubes containing EDTA and used for preparation of stained blood smears for light microscopy and for determination of the PCV. Serum samples were collected from each animal before immunization, weekly until the cattle were challenge-exposed and daily after cattle developed parasitemia as a result of challenge-exposure. Serum samples were stored at −70° C. until tested by competitive ELISA and Western blots.

6. Characterization of the immune response in vaccinated cattle by competitive ELISA and Western blots. Antibody responses of all immunized and control cattle at two weeks after the last immunization to MSP1a, MSP1b and MSP5 were determined using ELISAs specific for detection of antibodies to each of these MSPs. Antibody responses of all immunized and control cattle at two weeks after the last immunization to MSP1a and MSP1b were also analyzed by Western blot. One hundred micrograms of recombinant MSP1a or MSP1b were loaded in an 8% polyacrylamide gel. SDS-PAGE gels were transferred to a nitrocellulose membrane. The membrane was blocked with 5% skim milk for 1 hr at room temperature. Sera from immunized cattle was diluted 1:200 in TBS. Serum from an uninfected bovine was included as a negative control. All sera were incubated with the membrane for 1 hr at room temperature using a Mini-Protean II Multi-screen (BioRad, USA). The membrane was washed 3 times with TBST and incubated for 1 hr at room temperature with goat anti-rabbit IgG alkaline phosphatase conjugate (KPL, USA) diluted 1:10,000. The membrane was washed again and the color developed using Sigma Fast BCIP/NBT alkaline phosphatase substrate tablets. The membrane was then examined for recognition of the bands corresponding to MSP1a and MSP1b.

7. Statistical analysis. For the analysis of results from the immunization experiment, pairwise comparisons (Student's t test) were conducted to compare results between cattle immunized with antigen preparations and the controls. Parameters analyzed included the prepatent period (days), the peak percent parasitized erythrocytes (PPE) and the percent reduction in the packed cell volume (PCV). Mean antibody levels were compared using an ANOVA test.

8. Results. Antibody titers against MSP1a, MSP1b and MSP5 in immunized cattle peaked two weeks after the last immunization. The immune response against MSP1a, MSP1b and MSP5 was analyzed by Western blot. Cattle immunized with recombinant antigen preparations responded to recombinant proteins included on each preparation (FIG. 1). Cattle immunized with tick cell derived *A. marginale* antigens and with infected erythrocytes-derived antigens recognized primarily MSP1b or MSP1a, respectively (FIG. 1).

Protection was evaluated using the reduction in PCV, the PPE and the prepatent period. No differences were observed in the prepatent period. The PPE was reduced in cattle immunized with MSP1a, MSP1b, the combination of recombinant antigens with infected tick cells-derived antigens and in animals immunized with infected erythrocytes-derived antigens as shown in Table 1.

TABLE 1

| Group | Peak Parasitemia (%) | | |
|---|---|---|---|
| | Ave | SD | P |
| MSP1 | 5.5 | 2.8 | 0.13 |
| 1a + 1b | 6.0 | 1.6 | 0.14 |
| 1a | 4.8 | 0.6 | 0.03 |
| 1b | 3.9 | 1.0 | 0.01 |
| TC | 4.1 | 2.3 | 0.03 |
| 1a + TC | 4.7 | 1.4 | 0.03 |
| 1b + TC | 3.9 | 0.8 | 0.01 |
| RBC | 2.7 | 1.1 | 0.004 |
| Saline | 5.5 | 1.4 | 0.08 |
| Cells | 7.4 | 2.3 | — |

Figure 2:
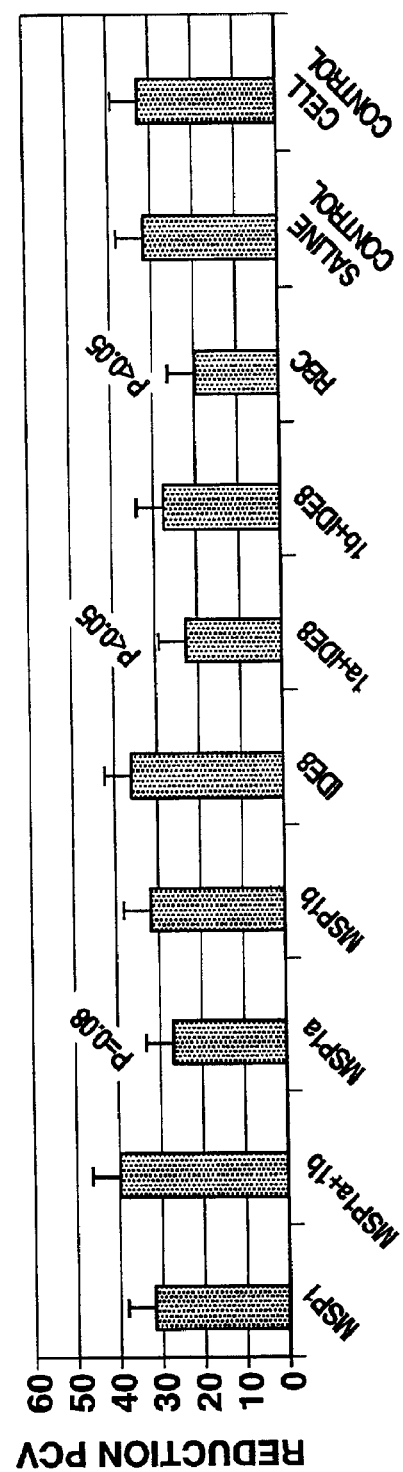
FIG. 2 is a graphical illustration of the reduction in PCV achieved by various combinations of antigens and controls in connection with the experimental results reported herein.

The reduction in PCV, associated with clinical signs, was significantly reduced in cattle immunized with MSP1a combined with infected tick cell-derived antigens and in cattle immunized with erythrocyte-derived antigens (See FIG. 2, wherein Reduction PCV=[(Ave Start PCV-Lowest PCV)/Start PCV]×100).

The results of these experiments demonstrated that:
a. Cattle immunized with infected tick cell-derived antigens had a preferential recognition for MSP1b while cattle immunized with erythrocyte-derived antigens showed a bias toward MSP1a. The bias in the antibody response against MSP1a or MSP1b in cattle immunized with *A. marginale* antigens from IDE8 tick cells or bovine erythrocytes suggests that the MSP1 complex exposure on the surface of parasites may vary during multiplication on the tick and mammalian hosts;
b. The immunization with the MSP1 complex or with MSP1a and MSP1b together did not protect cattle after challenge with *A. marginale* despite that cattle responded to both antigens; and
c. Cattle with a predominant immune response against MSP1a (groups immunized with MSP1a, MSP1a plus infected tick cell-derived antigens and infected erythrocyte-derived antigens) were protected against *A. marginale* infection as demonstrated by the lower reduction in PCV.

It can thus be appreciated that the utilization of recombinant MSP1a in vaccines provides an advantageous mechanism to achieve resistance in cattle against *A. marginale* infection. Whereas erythrocyte-derived *A. marginale* is disadvantaged due to cost, difficulties in purifying antigen from bovine membranes, problems with preventing pathogen contamination and difficulties in standardization, recombinant MSP1a may be readily and cost effectively prepared in a standardized, pure form free of bovine erythrocyte membranes and antigens that might result in formation of an immune response to bovine blood cells.

EXAMPLE 3

Function of MSP1a Tandem Repeats in Adhesion to Host Cell Receptors

1. Construction, expression in *E. coli* and characterization of wild type MSP1a and mutants. A MSP1a (Oklahoma isolate msp1α clone pen1 [14]) mutant lacking the tandem repeats was constructed by PCR. Oligonucleotide primers RI0R (5'-CCGAATTCCATGTTAGCGGCTAATTGGCGG-CAAGAGATGCG-3') (SEQ. ID NO: 5) and MSP1a3BII (5'-CCAGATCTCTTTACGCCGCCGCCTGCGCC-3') (SEQ. ID NO: 6) were designed to amplify the msp1α gene lacking 6 amino acids preceding the repeats and the tandem repeats in a 50 μl volume PCR (0.2 μM each primer, 1.5 mM $MgSO_4$, 0.2 mM dNTP, 1X AMV/Tfl reaction buffer, 5 u Tfl DNA polymerase) employing the Access RT-PCR system (Promega, USA). Reactions were performed in an automated DNA thermal cycler (Eppendorf MASTERCYCLER® personal, USA) for 35 cycles. After an initial denaturation step of 30 sec at 94° C., each cycle consisted of a denaturing step of 30 sec at 94° C. and an annealing-extension step of 2.5 min at 68° C. The program ended by storing the reactions at 4° C. The primers introduced an ATG initiation codon and Eco RI and BgI II restriction sites for cloning into the pFLAG-CTC expression vector (Sigma). The resulting plasmid pAF0R1 was transformed into *E. coli* JM109 and induced for expression of mutant MSP1a as previously reported for MSP1a [14]. For the expression of MSP1a (Oklahoma isolate msp1 α clone per1 [14]) tandem repeats in *E. coli*, this region was amplified using oligonucleotide primers RNOKBS5 (5'-GAGATCTGCTGATGGCTCGTCAGCGGG-3') (SEQ. ID NO: 7) and RNOKBS3 (5'-GGTCGACCCT-GATTGAGACGATGTACTGGCC-3') (SEQ. ID NO: 8). The PCR was conducted as previously described but with amplification cycles consisting of a denaturing step of 30 sec at 94° C., an annealing step of 30 sec at 58° C. and an extension step of 1 mm at 68° C. The 5' and 3' amplification primers contained Bgl II and Sal I restriction sites, respectively, for cloning into pFLC1b [14] for expression in *E. coil* as a fusion peptide to the COOH-terminus of MSP1b (locus β1, Oklahoma isolate). The resulting plasmid pF1bRNO4 was transformed into *E. coli* JM109 and induced for expression of mutant MSP1b>MSP1a-repeats protein as previously reported for MSP1b [14]. All constructs were sequenced at the Core Sequencing Facility, Department of Biochemistry and Molecular Biology, Noble Research Center, Oklahoma State University using ABI Prism dye terminator cycle sequencing protocols developed by Applied Biosystems (Perkin-Elmer Corp., Foster City, Calif.).

Expression of recombinant mutant proteins was assayed by SDS-PAGE, Western blot or live-cell immunofluorescence assay as previously reported [14]. The hemagglutination of bovine erythrocytes and adhesion to cultured IDE8 tick cells of recombinant *E. coli* expressing the wild type and mutant proteins was evaluated in a microtitre hemagglutination and *E. coli* recovery adhesion assays, respectively, as reported [14].

2. Results. To study the function and structural organization of tandem repeated peptides in MSP1a we selected a recent *A. marginale* field isolate from Oklahoma that is tick-transmissible and for which we have cloned and characterized MSP1a and MSP1b. A recombinant mutant MSP1a was constructed lacking the tandem repeated peptides and expressed in *E. coli*. The recombinant mutant protein was expressed at high levels and was secreted to the *E. coli* membrane as shown by live-cell immunofluorescence. Nevertheless, the adhesion to cultured IDE8 tick cells of recombinant *E. coli* expressing the mutant protein was abolished when compared to the wild type MSP1a (Table 2). To demonstrate that the MSP1a repeats were not only necessary but sufficient to confer adhesion of recombinant *E. coli* to tick cells, we then constructed a chimeric protein containing the MSP1a tandem repeated peptides fused to the COOH-terminus of the MSP1b. MSP1b did not confer an adhesive phenotype when expressed in *E. coli* (Table 3). However, *E. coli* expressing the chimeric protein adhered to cultured IDE8 tick cells at levels comparable to the wild type MSP1a-expressing *E. coli* (Table 3).

The capacity of MSP1a to hemagglutinate bovine erythrocytes was also mediated by the tandem repeats. Recombinant *E. coli* expressing the MSP1a lacking the tandem repeats were unable to hemagglutinate bovine erythrocytes (Table 2) while the chimeric MSP1b>MSP1a-repeats protein expressed in *E. coli* conferred to recombinant bacteria a higher hemagglutination capacity (Table 3) when compared to wild type MSPs.

TABLE 2

Hemagglutination of bovine erythrocytes and adhesion to cultured tick IDE8 cells by recombinant *E. coli* expressing *A. marginale* (Oklahoma isolate) MSP1a wild type and mutant protein without repeats

| | Plasmid carried by recombinant *E. coli* | | | |
|---|---|---|---|---|
| | pFLC1a | pAF0R1 | p33 | No plasmid |
| Relevant protein expressed | MSP1a | MSP1a-no repeats mutant | None | None |
| No. of CFU (mean ± SD) recovered from IDE8 cells (N = 3) | 500 ± 141 | 14 ± 18 | 231 ± 129 | 0 |
| Average fold increase over p33 control | 2 | — | — | — |
| P (Student's t-Test) | 0.05 | — | — | — |
| Average fold decrease over MSP1a (OK) | — | 36 | — | — |
| P (Student's t-Test) | — | 0.02 | — | — |
| Hemagglutination of bovine erythrocytes (N = 3)[a] | 1 | 0 | 0 | 0 |

[a]0, no hemagglutination;
1, weak hemagglutination;
2, moderate hemagglutination;
3, near maximum hemagglutination;
4, maximum hemagglutination [7].

TABLE 3

Hemagglutination of bovine erythrocytes and adhesion to cultured IDE8 tick cells of *E. coli* expressing wild type MSP1a or MSP1b (Oklahoma isolate) and MSP1b > MSP1a-repeats mutant proteins

| | Plasmid carried by recombinant *E. coli* | | |
|---|---|---|---|
| | pFLC1a | pFLC1b2 | pF1bRNO4 |
| Relevant protein expressed | MSP1a | MSP1b | MSP1b > MSP1a-repeats |
| No. of CFU recovered from IDE8 cells (Ave ± SD) (N = 2) | 975 ± 742 | 18 ± 17 | 530 ± 325 |
| Average fold increase over pFLC1b2 (MSP1b) | 54 | — | 29 |
| Hemagglutination of bovine erythrocytes (N = 2)[a] | 1 | 4 | 5 |

[a]Plates were incubated for 2 hours at 4° C. and results scored essentially as reported by McGarey and Allred [7]:
0, no hemagglutination;
1, weak hemagglutination;
2, moderate hemagglutination;
3, near maximum hemagglutination;
4, maximum hemagglutination;
5, maximum hemagglutination in 1 hour.

Accordingly, it can be appreciated that subunits derived from MSP1a are useful as well in the inventive vaccine compositions. The inclusion of MSP1a region(s) effecting MSP1a biological function could enhance the host immune response directed against relevant immunoprotective epitopes.

The preparation of vaccines utilizing as distinct antigenic components MSP1a is easily accomplished using well known methods and techniques. The vaccine and/or antigen preparation is combined into a formulation in an amount effective to provide for a protective immune response against infection with *A. marginale*. A protective immune response against *A. marginale* decreases the clinical signs of anaplasmosis. Clinical symptoms of anaplasmosis include a reduction in packed red cell volume of about 25 to 80% and parasitemia of the red blood cells of about 15 to 70%. A decrease in the symptoms of anaplasmosis includes prevention of the reduction in the packed red cell volume and a decrease in percent parasitemia. Preferably, a protective response includes packed red cell volume change of 25% or less compared with control animals and/or a decrease in parasitemia to about 5 to 25% of the red blood cells or less depending on the conditions. Measurements of packed red cell volume and percent parasitemia are conducted using standard methods. Vaccine preparations are combined with physiologically acceptable carriers to form vaccines. The preferred physiologically acceptable carrier is an oil-based adjuvant.

Preferably, the inventive vaccine formulation is set to contain about 100 micrograms of recombinant antigens associated to *E. coil* membranes in an oil-based adjuvant such as XTEND® III (Grand Laboratories, Larchwood, Iowa).

The vaccines may be administered by a variety of routes including intravenously, intraperitoneally, intramuscularly, and subcutaneously. The preferred route of administration is subcutaneous. The vaccine can be administered in a single dose or multiple doses until a protective effect is achieved.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

Bibliography

Each of the following publicly available documents is incorporated herein by reference.

[1] Kocan K M, Blouin E F, Barbet A F. Anaplasmosis control: past, present and future. Ann NY Acad Sci, 2000; 916: 501–509.

[2] Barbet A F, Palmer G H, Myler P J, McGuire T C. Characterization of an immunoprotective protein complex of *Anaplasma marginale* by cloning and expression of the gene coding for polypeptide AM 105L. Infect Immun1987; 55: 2428–2435.

[3] Viseshakul N, Kamper S, Bowie M V, Barbet A F. Sequence and expression analysis of a surface antigen gene family of the rickettsia *Anaplasma marginale*. Gene 2000; 253: 45–53.

[4] Palmer G H, Waghela S D, Barbet A F, Davis W C, McGuire T C. Characterization of a neutralization-sensitive epitope on the AM 105 surface protein of *Anaplasma marginale*. J Parasitol 1987; 17: 1279–1285.

[5] Palmer G H, Barbet A F, Cantor G H, McGuire T C. Immunization of cattle with the MSP-1 surface protein complex induces protection against a structurally variant *Anaplasma marginale* isolate. Infect Immun 1989; 57: 3666–3669.

[6] McGarey D J, Barbet A F, Palmer G H, McGuire T C, Allred D R. Putative adhesins of *Anaplasma marginale*: major surface polypeptides 1*a* and 1*b*. Infect Immun 1994; 62: 4594–4601.

[7] McGarey D J, Allred D R. Characterization of hemagglutinating components on the *Anaplasma marginale* initial body surface and identification of possible adhesins. Infect Immun 1994; 62: 4587–4593.

[8] Munderloh U G, Blouin E F, Kocan K M, Ge N L. Establishment of the tick (Acari: Ixodidae)-bone cattle pathogen *Anaplasma marginale* (Rickettsiales: Anaplasmataceae) in tick cell culture. J Med Ent 1996; 33: 656–664.

[9] Blouin E F, Barbet A F, Jooyoung Yi, Kocan K M, Saliki J T. Establishment and characterization of an Oklahoma isolate of *Anaplasma marginale* in cultured *Ixodes scapularis* cells. Vet Parasitol 1999; 87: 301–313.

[10] Blouin E F, Kocan K M. Morphology and development of *Anaplasma marginale* (Rickettsiales: Anaplasmataceae) in cultured *Ixodes scapularis* (Acari:Ixodidae) cells. J Med Entomol 1998; 35: 788–797.

[11] Barbet A F, Blentlinger R, Jooyoung Yi, Lundgren A M, Blouin E F, Kocan K M. Comparison of surface proteins of *Anaplasma marginale* grown in tick cell culture, tick salivary glands, and cattle. Infect Immun1999; 67:102–107.

[12] Oberle S M, Palmer G H, Barbet A F, McGuire T C. Molecular size variations in an immunoprotective protein complex among isolates of *Anaplasma marginale*. Infect Immun 1988; 56: 1567–1573.

[13] Allred D R, McGuire T C, Palmer G H, Leib S R, Harkins T M, McElwain T F, Barbet A F. Molecular basis for surface antigen size polymorphisms and conservation of a neutralization-sensitive epitope in *Anaplasma marginale*. Proc Natl Acad Sci USA 1990; 87: 3220–3224.

[14] de la Fuente, J., Garcia-Garcia, J. C., Blouin, E. F., Kocan, K. M. Differential adhesion of major surface proteins 1*a* and 1*b* of the ehrlichial cattle pathogen *Anaplasma marginale* to bovine erythrocytes and tick cells. Int. J. Parasitol. 2001; 31: 145–153.

[15] de la Fuente, J., van den Bussche, R. A., Kocan, K. M. Molecular phylogeny and biogeography of North American isolates of *Anaplasma marginale*. Veterinary Parasitology 2001; 97: 65–76.

What is claimed is:

1. A vaccine composition for inducing an immune response in a ruminant, said vaccine composition comprising recombinant MSP1a in combination with an immunogen derived from A. marginale, wherein said immunogen is not isolated or recombinant MSP1b and said vaccine composition further comprises a pharmaceutically acceptable carrier or diluent.

2. The vaccine according to claim 1, wherein said immunogen is tick cell culture derived A. marginale.

3. The vaccine according to claim 2, wherein said tick cell culture comprises Ixodes scapularis tick cell line IDE8.

4. The vaccine according to claim 1, wherein said recombinant MSP1a is from the Oklahoma isolate of A. marginale.

5. The vaccine according to claim 4, wherein said immunogen is derived from the Oklahoma isolate of A. marginale.

6. A method for inducing a protective immune response in a ruminate against A. marginale comprising administering to the ruminant an effective dose of the vaccine composition of claim 1.

7. The method according to claim 6, wherein said dose comprises approximately 100 μg of said recombinant MSP1a.

8. The method according to claim 6, wherein said immunogen of said vaccine composition is tick cell culture derived A. marginale.

9. The method according to claim 8, wherein said tick cell culture comprises Ixodes scapularis tick cell line IDE8.

10. The method according to claim 6, wherein said recombinant MSP1a of said vaccine composition is from the Oklahoma isolate of A. marginale.

11. The method according to claim 10, wherein said immunogen of said vaccine composition is derived from the Oklahoma isolate of A. marginale.

12. The method according to claim 8, wherein said dose comprises approximately $2 \times 10^{10}$ of said tick cell culture derived A. marginale.

13. The vaccine composition according to claim 1, wherein said recombinant MSP1a is associated to E. coli membrane fractions.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: artificial
<220> FEATURE:
<223> OTHER INFORMATION: oligonucleotide primer

<400> SEQUENCE: 1
gcattacaac gcaacgcttg ag                                             22

<210> SEQ ID NO 2
<211> LENGTH: 22
<212> TYPE: DNA
<213> ORGANISM: artificial
<220> FEATURE:
<223> OTHER INFORMATION: oligonucleotide primer

<400> SEQUENCE: 2
gctttacgcc gccgcctgcg cc                                             22

<210> SEQ ID NO 3
<211> LENGTH: 30
<212> TYPE: DNA
<213> ORGANISM: artificial
<220> FEATURE:
<223> OTHER INFORMATION: oligonucleotide sequence

<400> SEQUENCE: 3
ccgctcgaga tgttagcgga gtatgtgtcc                                     30

<210> SEQ ID NO 4
<211> LENGTH: 24
<212> TYPE: DNA
<213> ORGANISM: artificial
<220> FEATURE:
<223> OTHER INFORMATION: oligonucleotide primer

<400> SEQUENCE: 4
```

-continued

```
gaagatctcg ccgccgcctg cgcc                                              24

<210> SEQ ID NO 5
<211> LENGTH: 41
<212> TYPE: DNA
<213> ORGANISM: artificial
<220> FEATURE:
<223> OTHER INFORMATION: oligonucleotide primer

<400> SEQUENCE: 5
ccgaattcca tgttagcggc taattggcgg caagagatgc g                           41

<210> SEQ ID NO 6
<211> LENGTH: 29
<212> TYPE: DNA
<213> ORGANISM: artificial
<220> FEATURE:
<223> OTHER INFORMATION: oligonucleotide primer

<400> SEQUENCE: 6
ccagatctct ttacgccgcc gcctgcgcc                                         29

<210> SEQ ID NO 7
<211> LENGTH: 27
<212> TYPE: DNA
<213> ORGANISM: artificial
<220> FEATURE:
<223> OTHER INFORMATION: oligonucleotide primer

<400> SEQUENCE: 7
gagatctgct gatggctcgt cagcggg                                           27

<210> SEQ ID NO 8
<211> LENGTH: 31
<212> TYPE: DNA
<213> ORGANISM: artificial
<220> FEATURE:
<223> OTHER INFORMATION: oligonucleotide primer

<400> SEQUENCE: 8
ggtcgaccct gattgagacg atgtactggc c                                      31
```